(12) United States Patent
Matsutani

(10) Patent No.: US 7,069,757 B2
(45) Date of Patent: Jul. 4, 2006

(54) TWISTING APPARATUS FOR ULTRAFINE RECTANGULAR BAR

(75) Inventor: Kanji Matsutani, Tochigi-ken (JP)

(73) Assignee: Mani, Inc., Tochigi-ken (JP)

( * ) Notice: Subject to any disclaimer, the term of this patent is extended or adjusted under 35 U.S.C. 154(b) by 149 days.

(21) Appl. No.: 10/786,122

(22) Filed: Feb. 26, 2004

(65) Prior Publication Data
US 2004/0177665 A1    Sep. 16, 2004

(30) Foreign Application Priority Data
Feb. 26, 2003  (JP) .............................. 2003-048773

(51) Int. Cl.
*B21B 15/02*  (2006.01)
(52) U.S. Cl. .................. 72/64; 72/65; 72/298; 72/299; 72/371
(58) Field of Classification Search .................... 72/64, 72/65, 299, 371, 298; 76/102
See application file for complete search history.

(56) References Cited

U.S. PATENT DOCUMENTS

| | | | |
|---|---|---|---|
| 3,427,844 A * | 2/1969 | Bergstrom | 72/64 |
| 3,427,845 A * | 2/1969 | Evans | 72/64 |
| 4,604,884 A * | 8/1986 | Matsutani | 72/299 |

FOREIGN PATENT DOCUMENTS

| JP | 61-53059 | 11/1986 |
|---|---|---|
| JP | 62-22733 | 5/1987 |

OTHER PUBLICATIONS

English Abstract of JP 601290942, published Jul. 10, 1985.
English Abstract of JP 60016324, published Jan. 28, 1985.

* cited by examiner

Primary Examiner—Derris H. Banks
Assistant Examiner—Hung C. Le
(74) Attorney, Agent, or Firm—Townsend & Banta

(57) ABSTRACT

The present invention relates to a twisting apparatus for an ultrafine rectangular bar, comprising: a chuck; chuck driving means; at least two vise clamps each of the vise clamps having a pressing surface capable of contacting to a side surface of the ultrafine rectangular bar; and vise clamp driving means. The chuck driving means and the vise clamp driving means are so controlled that, after the proximal end of the ultrafine rectangular bar is held by the chuck where the vise clamps are placed closely to the ultrafine rectangular bar, the chuck disengages the ultrafine rectangular bar when the vise clamps contact to the ultrafine rectangular bar and then engages again the ultrafine rectangular bar, in a ease where the vise clamps are approached closely to the ultrafine rectangular bar held by the chuck to twist the ultrafine rectangular bar upon isolating, as rotated correlatively, the chuck and the vise clamps from each other.

5 Claims, 6 Drawing Sheets

FIG.6
(a)
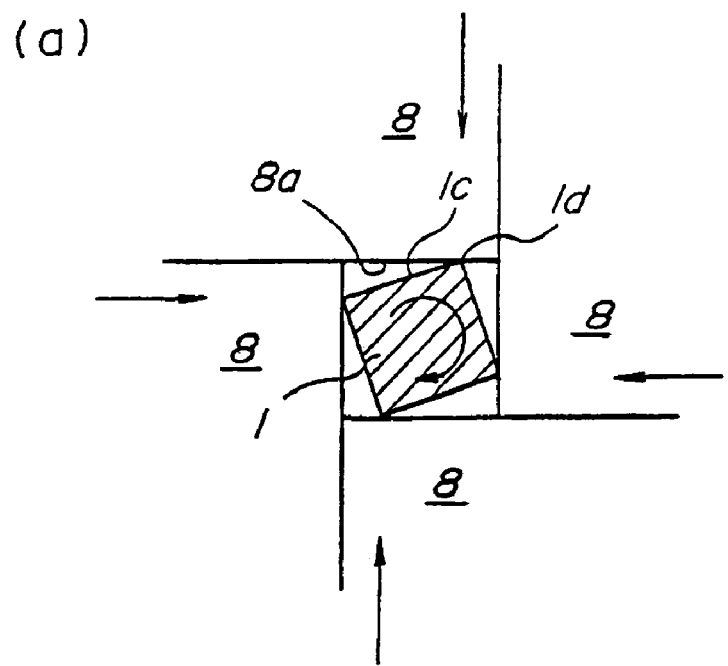
(b)
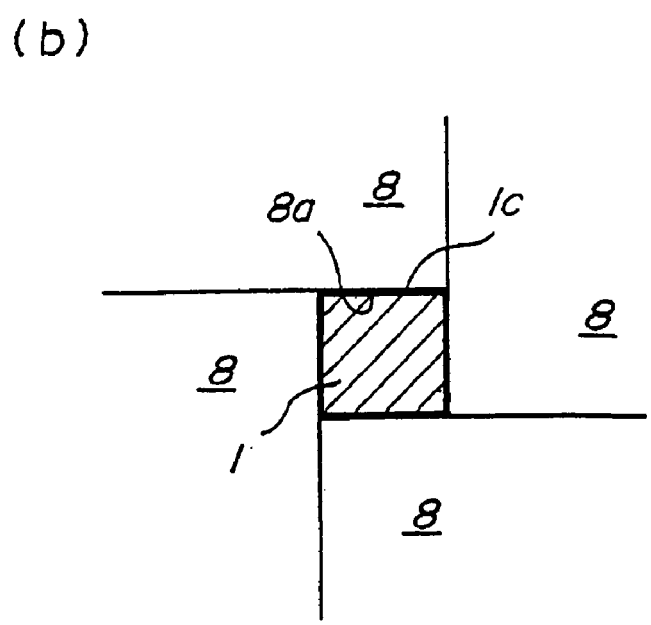

TWISTING APPARATUS FOR ULTRAFINE RECTANGULAR BAR

BACKGROUND OF THE INVENTION

1. Field of the Invention

This invention relates to a twisting apparatus for ultrafine rectangular bar whose cross section is formed in a rectangular shape such as a triangle or square to be formed in a spiral shape upon twisting the ultrafine rectangular bar.

2. Description of Related Art

In dental treatments, while a surface of a calcified root canal wall is cut, cutting debris or contents filled in the root canal are removed to expose a new surface of the root canal wall and to form the root canal. Endodontic devices including files and reamers having different diameter sizes are provided as instruments for forming such root canals. Some of those files and reamers are provided in having a rectangular cross-sectional shape and different diameter sizes, which are selectable according to the procedure of the treatment.

For example, a K-file is provided in having a cross section in a triangle or square shape, having a work portion formed in a spiral shape with a relatively narrow pitch made by a twisting process, and having a function to shave the root canal wall mainly upon pushing and pulling manipulations and to remove the shaved debris and contents. A reamer is provided in having a cross section in a square shape, having a work portion formed in a spiral shape with a relatively wide pitch made by a twisting process, and having a function to shave the root canal wall mainly upon rotational manipulations and to remove the shaved debris and contents.

Such K-files and reamers are standardized having diameters at a distal end of 0.02 pitch between 0.06 mm and 0.10 mm, 0.05 pitch between 0.10 mm and 0.60 mm, and 0.10 pitch at 0.60 mm or higher but up to 1.40 mm. Accordingly, the materials are formed as square bars having the same cross section as the targeted products.

The apparatus for twisting ultrafine rectangular bars having such diameters and cross-sectional shapes includes a chuck for holding the ultrafine rectangular bar as a material, and a plurality of vise clamps for restricting the ultrafine rectangular bar in contact with the side surface of the bar. After the ultrafine rectangular bar having the same cross-sectional shape and diameter as the targeted products is held by the chuck, the ultrafine rectangular bar is made in contact with the vise clamps, and then, the bar can be twisted by rotating correlatively the chuck and the vise clamps and isolating the chuck and the vise clamps from each other as restricting the ultrafine rectangular bar with the vise clamps (see, e.g., Japanese Patent Publication Nos. JB-61-53059, JB-62-22733).

With the above twisting apparatus, however, the positional relation between the corner portion of the ultrafine rectangular bar held by the chuck and the vise clamp is not controlled at all. That is, when the vise clamp is made coming closely to the ultrafine rectangular bar, what portion of the ultrafine rectangular bar comes in contact with the vise clamp is not managed. Therefore, when the twisting work for the ultrafine rectangular bar is started, the twisting starting position may be deviated in the axial direction between starting where the vise clamp contacts with a plane and starting where the vise clamp contacts with a corner portion, so that there arises a problem that the length of the twisting portion become not unified.

SUMMARY OF THE INVENTION

It is an object of the invention to provide an ultrafine rectangular bar twisting apparatus making stable the twisting start position at each ultrafine rectangular bar and realizing unified lengths of the twisting portion.

A twisting apparatus for an ultrafine rectangular bar to solve the above problems according to the invention includes: a chuck for holding a proximal end of the ultrafine rectangular bar; chuck driving means for holding or releasing the proximal end of the ultrafine rectangular bar by driving the chuck; at least two vise clamps structured to contact with and isolated from the ultrafine rectangular bar held by the chuck, each of the vise clamps having a pressing surface capable of contacting to a side surface of the ultrafine rectangular bar; vise clamp driving means for driving the vise clamps to move the vise clamps to contact with and isolated from the ultrafine rectangular bar; moving means for correlatively moving the chuck and the vise clamps along the axial center of the ultrafine rectangular bar held by the chuck; and rotating means for correlatively rotating the chuck and the vise clamps around the axial center of the ultrafine rectangular bar held by the chuck, wherein the chuck driving means and the vise clamp driving means are so controlled that, after the proximal end of the ultrafine rectangular bar is held by the chuck where the vise clamps are placed closely to the ultrafine rectangular bar, the chuck disengages ultrafine rectangular bar when the vise clamps contact to the ultrafine rectangular bar and then engages again the ultrafine rectangular bar, in a case where the vise clamps are approached closely to the ultrafine rectangular bar held by the chuck to twist the ultrafine rectangular bar upon isolating, as rotated correlatively, the chuck and the vise clamps from each other.

With the above twisting apparatus for the ultrafine rectangular bar (hereinafter, simply referred to as "twisting apparatus"), the shape of the holding portion of the chuck is circle, and a corner of the ultrafine rectangular bar can correspond to a corner of the vise clamps when the vise clamps are made come closer and in contact with the ultrafine rectangular bar. That is, in a case where the corner of the ultrafine rectangular bar held by the chuck does not correspond to the corner of the vise clamps, the ultrafine rectangular bar rotates according to the shape of the vise clamps without disengaging from the chuck to render the corners of the vise clamps and the ultrafine rectangular bar face to each other upon disengaging the ultrafine rectangular bar from the chuck when the vise clamps come in contact with the ultrafine rectangular bar.

Accordingly, after the vise clamps contact to the ultrafine rectangular bar, the chuck is made closed again to hold the ultrafine rectangular bar, thereby rendering the ultrafine rectangular bar face to the vise clamps as facing to each other at the corners. Therefore, where the chuck and the vise clamps are isolated from each other at a prescribed rate as rotated correlatively, the ultrafine rectangular bar can be twisted with a prescribed pitch.

With the twisting apparatus thus described, it is preferable to provide a stopper contacting to the distal end of the ultrafine rectangular bar at a prescribed position on the axial center of the ultrafine rectangular bar held by the chuck, wherein the moving means, the chuck driving means, and the vise clamp driving means are so controlled that, where the vise clamp approaches closely and contacts to the ultrafine rectangular bar after the chuck holds the proximal end of the ultrafine rectangular bar, the chuck disengages from the ultrafine rectangular bar, and the distal end of the ultrafine rectangular bar is made in contact with the stopper upon moving correlatively the chuck and the stopper.

In the twisting apparatus, the length of the ultrafine rectangular bar, held by the chuck, from the chuck to the distal end is prescribed, and a corner of the ultrafine rectangular bar can correspond to a corner of the vise clamps. That is, where the chuck disengages from the ultrafine rectangular bar when the vise clamps approach to and come in contact with the ultrafine rectangular bar held by the chuck, and where the distal end of the ultrafine rectangular bar is made in contact with the stopper by correlatively moving the chuck and the stopper with respect to each other, the correlative position of the ultrafine rectangular bar with respect to the chuck is changed, where the chuck and the stopper are moving, according to the movements when the distal end of the ultrafine rectangular bar contacts to the stopper.

When the distance between the chuck and the stopper reaches a prescribed value, the ultrafine rectangular bar can be corresponded to the shape of the vise clamps, and the prescribed length can be held by stopping movements of the chuck and the stopper and by holding the ultrafine rectangular bar upon closing the chuck. Therefore, the position of starting the twisting process at the ultrafine rectangular bar can be regulated, so that the apparatus can treat good twisting products with unified lengths of the twisted portions.

With the above twisting apparatus, the vise clamp is preferably disposed at a position such that a portion of a clamp surface for clamping a side surface of the ultrafine rectangular bar can be in contact with a portion of the adjacent vise clamp.

Respective positions of the clamps can be adjusted along the exterior shape of the ultrafine rectangular bar when the vise clamps approach and come in contact with the ultrafine rectangular bar.

BRIEF DESCRIPTION OF THE DRAWINGS

The above and other objects, features and advantages of the present invention will become more apparent from the following description of the presently preferred exemplary embodiments of the invention taken in conjunction with the accompanying drawings, in which:

FIG. 6(a), 6(b) are illustrations showing maintenance work of the ultrafine rectangular bar with the vise clamps.

DETAILED DESCRIPTION OF PREFERRED EMBODIMENTS

Figure 1:
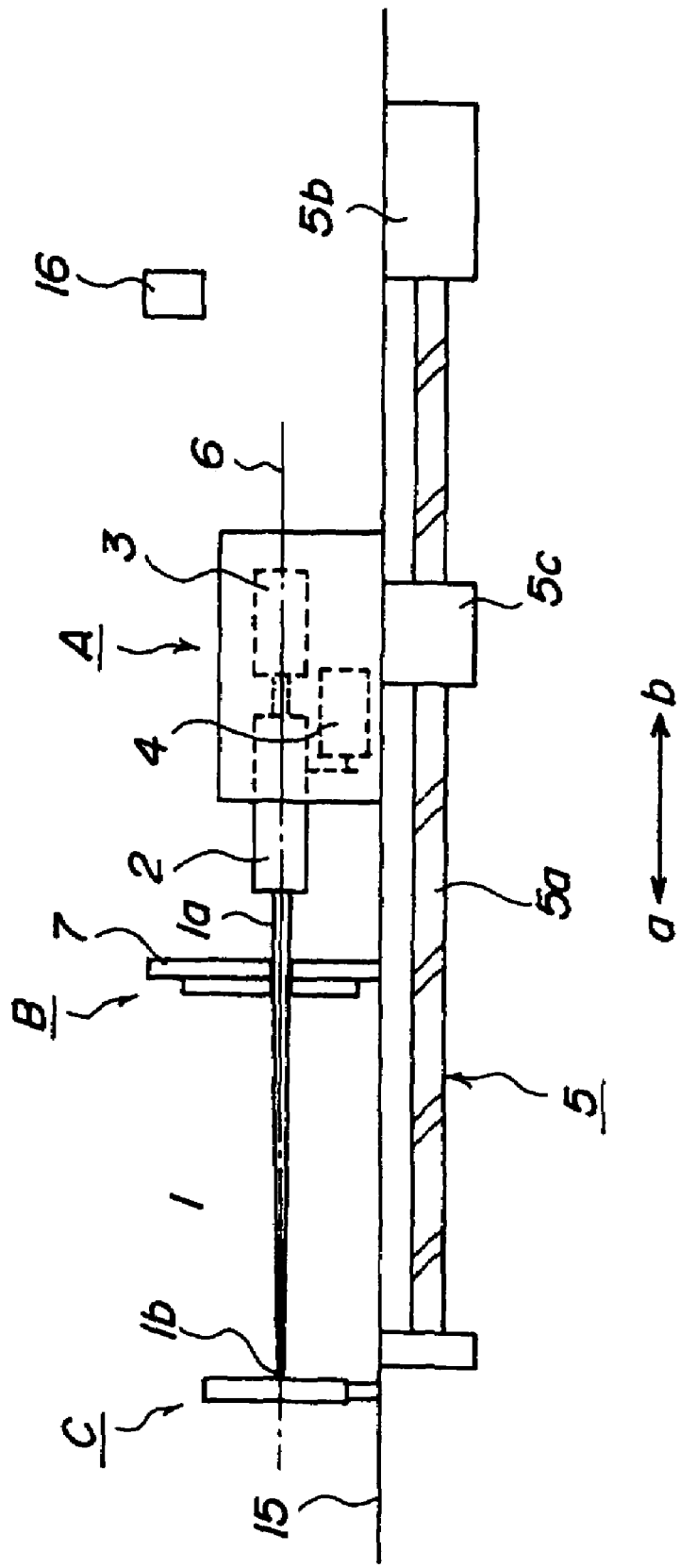
FIG. 1 is a schematic view showing the entire structure of a twisting apparatus according to the invention.
Figure 2:
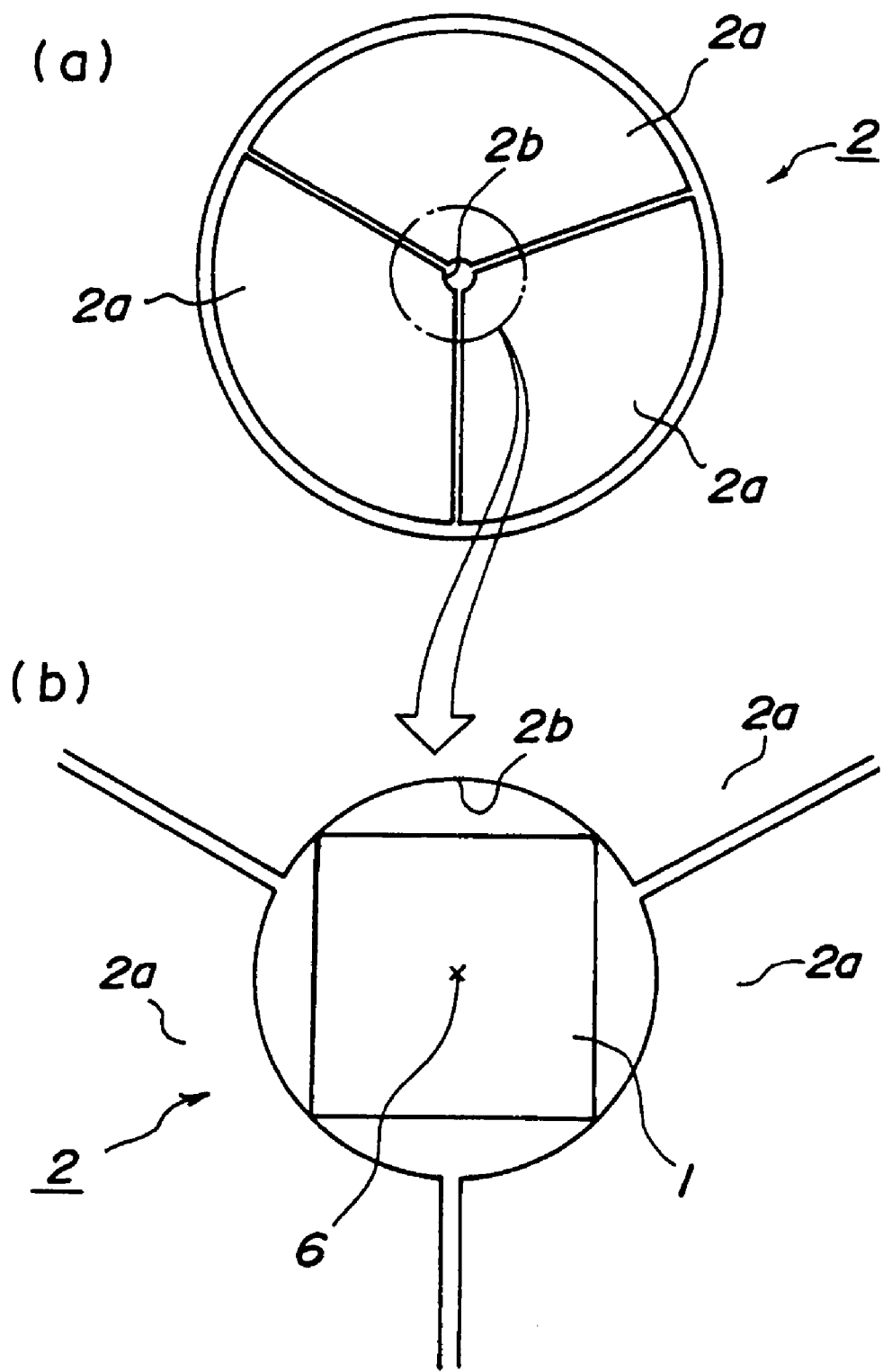
FIG. 2(a), 2(b) are illustrations describing a relation between a holding portion of a chuck and a cross-sectional shape of an ultrafine rectangular bar.
Figure 3:
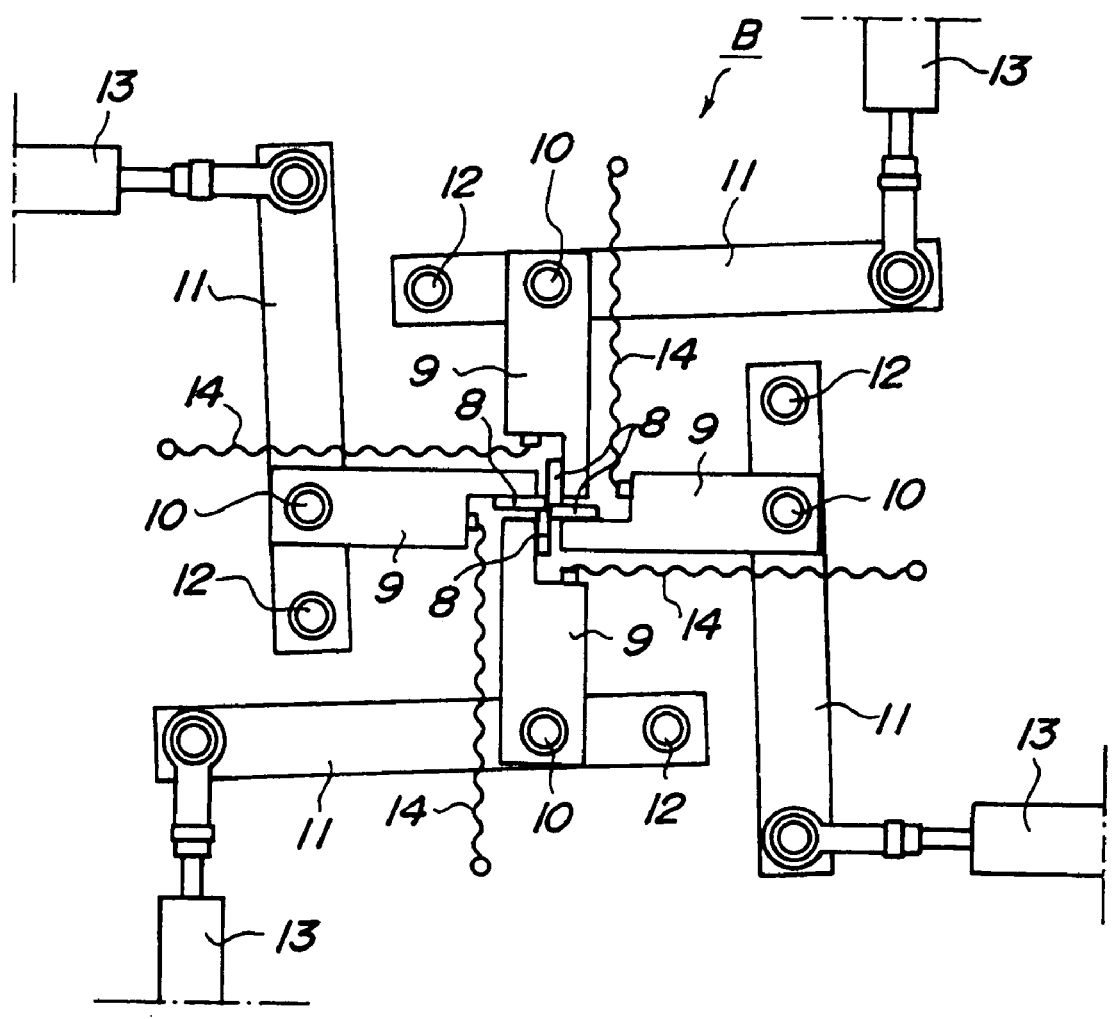
FIG. 3 is an illustration showing a structure of a vise clamp.
Figure 4:
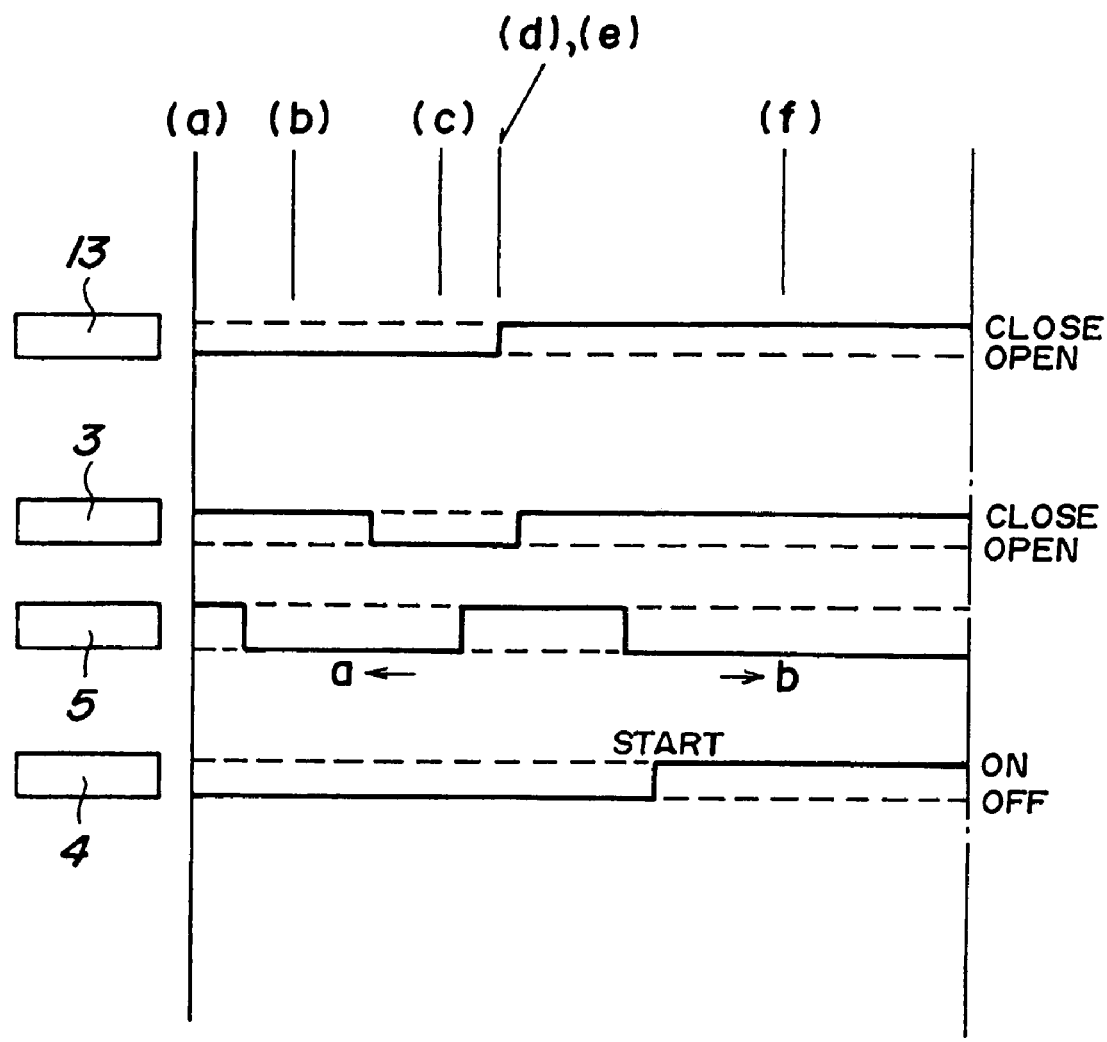
FIG. 4 is a timing chart for illustrating drive timings of essential portions in the twisting apparatus.

Hereinafter, referring to the drawings, preferred embodiments of the invented twisting apparatus are described. FIG. 1 is a schematic view showing the entire structure of a twisting apparatus according to the invention; FIG. 2(a), 2(b) are illustrations describing a relation between a holding portion of a chuck and a cross-sectional shape of an ultrafine rectangular bar; FIG. 3 is an illustration showing a structure of a vise clamp; FIG. 4 is a timing chart for illustrating drive timings of essential portions in the twisting apparatus; and FIG. 5(a) through FIG. 5(f) are process diagrams showing a twisting process sequence for the ultrafine rectangular bar with the twisting apparatus.

The twisting apparatus according to the invention is for twisting ultrafine rectangular bars formed in having very fine diameters and cross sections in triangle or square, and is allowing desirable manufacturing of reamers and files used as an endodontic instruments in dental treatments.

Particularly, the ultrafine rectangular bar is extended along the vise clamp by loosening the chuck's holding of the ultrafine rectangular bar in association with the contact of the vise clamp to the ultrafine rectangular bar where the chuck's holding position of the ultrafine rectangular bar is different from the disposed direction of the vise clamp. With this operation, the holding position of the ultrafine rectangular bar is made corresponding to the vise clamps, and the ultrafine rectangular bars, even where supplied in any orientation, can take the same orientation at a starting time of the twisting process with the vise clamps, where the chuck re-holds the ultrafine rectangular bar, so that the distances between the chuck and twisting starting position can be set equally.

By providing the vise clamps and the stopper to render the chuck holding the ultrafine rectangular bar correlatively approach to the stopper, by loosening the chuck's holding of the ultrafine rectangular bar when the distal end of the ultrafine rectangular bar contacts to the stopper, and by holding again the ultrafine rectangular bar with the chuck when the distance between the stopper and the chuck coincides to a prescribed amount, the length from the distal end of the ultrafine rectangular bar to the chuck can be maintained at a prescribed amount. Therefore, the portion at which the twisting process is made on the ultrafine rectangular bar can be set as having the same length.

The twisting apparatus shown in the drawings is constituted of a chuck portion A having a chuck 2 for holding the ultrafine rectangular bar 1, a vise clamp portion B for rendering a twisting process in contact with the ultrafine rectangular bar 1, and a stopper portion C. The ultrafine rectangular bar 1 held by the chuck portion A is positioned by the stopper portion C, and as the side surface of the ultrafine rectangular bar 1 is restricted by the vise clamp portion B and rotated, the chuck portion A and the vise clamp portion B are isolated correlatively, thereby allowing the process for twisting the ultrafine rectangular bars 1 having a prescribed length scope.

As described above, the chuck portion A and the stopper C are mutually come closely and isolated from each other, and the chuck portion A and the vise clamp portion B approach to and isolated from each other as rotated mutually. Accordingly, with the chuck portion A, the vise clamp portion B, and the stopper portion C, any one of those mechanisms is immovable whereas the others are movable. Which mechanism is immovable or movable is not particularly limited, but it is better off that those mechanisms are mutually, organically structured as movable and immovable.

In this embodiment, therefore, the chuck portion A is rotatable and can approach to and isolate from the vise clamp portion B, as well as the stopper portion C. The vise clamp portion B and the stopper portion C can be formed as entirely different structures, and the position of the stopper portion C is adjustable with respect to the vise clamp portion B upon assembling both on the same frame.

For what the ultrafine rectangular bar 1 is used is not specifically limited, but in this embodiment, the ultrafine rectangular bar 1 is targeting to be K-files and reamers used for endodontic treatment. These K-files and reamers are formed in having cross sections in an equilateral triangle or square and in respective sizes having diameters at the distal end of 0.02 pitch, 0.05 pitch, and 0.10 pitch between 0.06 mm and 1.40 mm. The ultrafine rectangular bar 1 is formed with a tapered shape having 2/100 gradient in a range of length at least 16 mm from the distal end 1b to the proximal end 1a.

The material of the ultrafine rectangular bar 1 is not specifically limited, and carbon steel or stainless steel can desirably be used. Particularly, as in this embodiment, when used for medical purposes, the tool inevitably has a proper flexibility and strength, so that materials such as annealed carbon steel or marten site based stainless steel, or austenite based stainless steel drawn in cooling, etc. can be selectively used.

The chuck portion A includes the chuck 2 for holding the proximal end of the fine rectangular bar 1, a chuck drive means 3 for engaging and disengaging the ultrafine rectangular bar 1 by opening and closing the chuck 2, and a rotary means 4 for rotating the chuck 2. The chuck portion A is structured to approach to and isolate from the vise clamp portion B and the stopper portion C by a moving means 5.

The chuck 2 is formed as a collet chuck having plural nails 2a, and holding surfaces 2b as inner surfaces of the nails 2a are formed to be a circle. The chuck drive means 3 has functions to hold or loosen the proximal end 1a of the ultrafine rectangular bar 1 upon moving the nails 2a along an axial center 6, and can use a linear drive member such as an air cylinder or solenoid.

Accordingly, even where the cross-sectional shape of the ultrafine rectangular bar 1 is in a triangle or square and where the bar is supplied in any position, the chuck 2 can hold the bar in a stable state. By loosening the chuck 2, the held ultrafine rectangular bar 1 can be rotated freely and moved in a direction of the axial center 6.

The rotary means 4 has a function to rotate the chuck 2 around the axial center 6 as a center at a preset rotation number, and any thing can be used as far as having this function. There are motors (electric motors, air motors, etc.) having a deceleration function as such a rotary means 4.

The moving means 5 is for reciprocally moving the chuck portion A along axial center 6, and any thing can be used as far as having this function. In this embodiment, the moving means 5 is constituted of a screw bar 5a disposed along the axial center, a motor 5b for driving the screw bar 5a, a nut member 5c secured to the chuck portion A in mesh with the screw bar 5a. It is to be noted that it is preferable to guarantee reciprocal movements with high accuracy by attaching the chuck portion A to a linear guide member available commercially.

The vise clamp portion B is structured at a frame 7 in a plate shape. The vise clamp portion B has a plurality of vise clamps 8 in a number corresponding to the cross-sectional shape of the ultrafine rectangular bar 1, and each vise clamp 8 is secured to a tip portion of an arm 9 and is arranged in a staggered manner as to contact to a side surface of another adjacent vise clamp 8. The arm 9 is attached pivotally around a pivot center 10 as a center to an arm 11, and the arm 11 is structured as pivotally movable around a pivot center 12 as a center. An air cylinder 13 serving as a drive means for vise clamp is attached to a free end side of the arm 12. A spring 14 is attached to the arm 9, and one vise clamp 8 is structured to be pushed to another adjacent vise clamp 8 by the urging force of the spring 14. It is to be noted that as shown in FIG. 6, the tip of the vise clamp 8 is a clamping surface 8a in a plane shape, and the clamp surface 8a comes in facial contact with a flat surface portion 1c of the ultrafine rectangular bar 1 when the vise clamp 8 approaches to the side surface of the ultrafine rectangular bar 1 and holds the ultrafine rectangular bar 1.

With the vise clamp portion B thus structured, the vise clamps 8 adjacent to each other contact to each other due to the urging force of the spring 14 when the vise clamps 8 are made closer to each other by drive of the air cylinder 13, and can be brought closely to the axial center 6 of the twisting apparatus surely as rendering the contact portions as a guide. While the twisting processing is made on the ultrafine rectangular bar 1, the vise clamp can follow the change of the diameter of the ultrafine rectangular bar 1 by continuously supplying compressed air to the air cylinder 13. Accordingly, the ultrafine rectangular bar 1 can be restricted always with an approximately constant force even where the ultrafine rectangular bar 1 is formed in a tapered shape with a diameter becoming smaller as goes from the proximal end 1a to the distal end 1b.

The stopper portion C is for limiting a protruding length of the ultrafine rectangular bar 1 from the chuck portion A to the distal end 1b by contacting to the distal end 1b of the ultrafine rectangular bar 1, and any thing can be used as far as having this function.

The chuck portion A, the vise clamp portion B, and the stopper portion C thus structured are disposed at respective positions on a frame 15. That is, the vise clamp portion B is disposed immovably at a prescribed position on the frame 15; the stopper portion C is arranged in a manner that the attached position is adjustable with respect to the frame 15 with the vise clamp portion B as a reference; the chuck portion A is arranged movably with respect to the frame (15).

Particularly, the stopper portion C has a set position from the vise clamp 8 of the vise clamp portion B in corresponding to the preset length of the twisting portion, and at this position, the vise clamp portion B and the stopper portion C are secured as not to shift the length between the vise clamp portion B and the stopper portion C. The immovable system is not specifically limited, and for example, the apparatus may use a system such that the stopper portion C can be secured to the frame 15, or that a screw bar, not shown, is attached to a frame 7 structuring the vise clamp portion B and is secured to the stopper C.

The distance between the vise clamp portion B and the stopper portion C corresponds to the distance between the distal end 1b of the ultrafine rectangular bar 1 and the twisting start position. The K-files and reamers as the dental treatment instruments are defined, under the ISO standard, to have a length of the twisting portion from the distal end of 16 mm or more, and therefore, in this embodiment, the interval between the vise clamp portion B and the stopper portion C is set 16 mm whereas the vise clamp portion B and the stopper portion C are respectively secured.

Control for holding and loosening operation of the ultrafine rectangular bar 1 by the chuck 2 at the chuck portion A, rotary control, moving control of the chuck portion A in a direction along the axial center 6, and operational control of the air cylinder 13 at the vise clamp portion B can be done with a microcomputer, sequencer, or timing cams.

In this embodiment, a sequencer is used as the controller, and operation sequence, and operation times, and the like of the respective operational portions are memorized in the sequencer. A sensor 16 is provided at a prescribed position of the frame 15 to detect the reference position of the chuck portion A, and the ultrafine rectangular bar 1 can be twisted by a series of operations with triggering upon a detected signal of the chuck portion A from the sensor 16.

Figure 5:
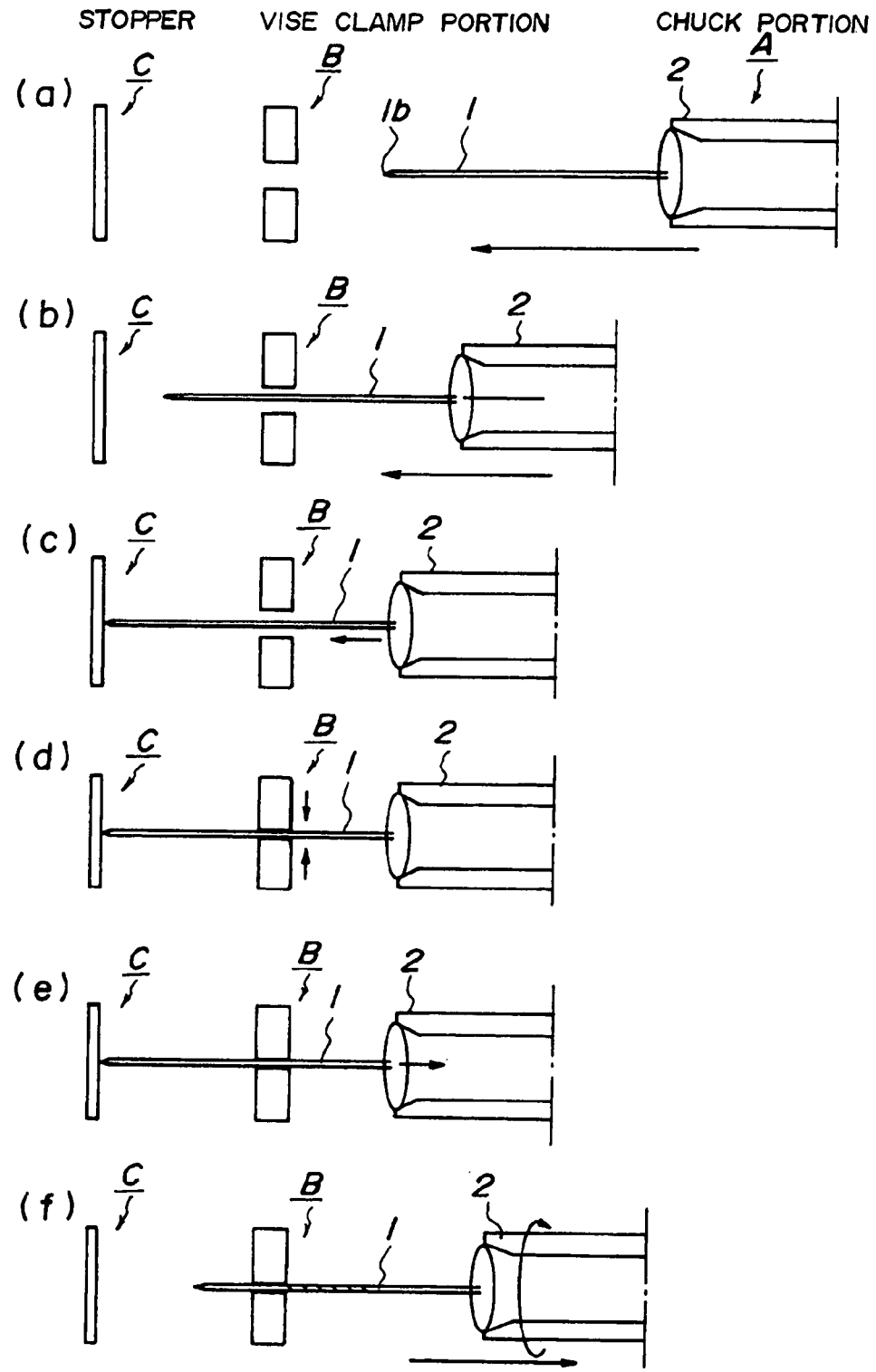
FIG. 5(a) through FIG. 5(f) are process diagrams showing a twisting process sequence for the ultrafine rectangular bar with the twisting apparatus.

Next, the twisting steps of the ultrafine rectangular bar 1 by the twisting apparatus thus structured are described in reference with FIG. 4, FIG. 5, and FIG. 6. It is to be noted that (a) through (f) in FIG. 4, FIG. 5 are shown as mutually related states.

The ultrafine rectangular bar 1 is supplied in an unmanaged manner to the chuck 2 structuring the chuck portion A, and the chuck 2 is driven by the chuck drive means 3 to render the ultrafine rectangular bar 1 in a held state. As shown in FIG. 4, FIG. 5(a), the chuck portion A is moved to the reference position detected by the sensor 16, and a series of operations begins upon the signal from the sensor 16.

Where the chuck 2 holds the ultrafine rectangular bar 1, the motor 5b structuring the moving means 5 drives, and according to this operation, as shown in FIG. 4, FIG. 5(b), the chuck portion A moves in a direction of arrow a in FIG. 1. The moving amount of the chuck portion A, or rotational amount of the motor 5b, is controlled by a timer signal from the sequencer. In a case where, e.g., a pulse motor is used as the motor 5b, the amount is controlled by the total number of the pulses transmitted to the motor 5b.

When the moving amount of the chuck portion A in the direction of arrow a reaches a prescribed length (timer signal, number of pulse signal, sensor, etc. may be arranged), as shown in FIG. 4, FIG. 5(c), the chuck 2 is so loosened by drive of the chuck driving means 3 as not to drop off the ultrafine rectangular bar 1. At that time, because the movement of the chuck portion A in the direction of arrow a is continued, the distal end of the ultrafine rectangular bar 1 comes in contact with the stopper portion C according to the continuation of the movement of the chuck portion A in the direction of arrow a and is prevented from further moving.

When the movement of the chuck portion A in the direction of arrow a ends, the protruding length of the ultrafine rectangular bar 1 held by the chuck 2 protruding from the chuck 2 is set uniformly by the position at which the chuck 2 stops and by the distance to the stopper portion C, so that the protruding length is hardly deviated, and so that stable protruding lengths can be realized.

In keeping the above state, as shown in FIG. 4 and FIG. 5(d), the air cylinder 13 is driven to render the vise clamps 8 structuring the vise clamp portion B approach to and come into contact with the ultrafine rectangular bar 1. FIG. 6(a) and FIG. 6(b) shows this situation. As shown in FIG. 6a the vise clamp 8 approaches to the ultrafine rectangular bar 1, and when the corner 1b of the ultrafine rectangular bar 1 contacts to the clamping surface 8a of the vise clamp 8, rotational force exerts to the ultrafine rectangular bar 1 according to the contact angle of the corner 1b of the ultrafine rectangular bar 1 with respect to the clamping surface 8a. Because the proximal end of the ultrafine rectangular bar 1 is disengaged from the chuck 2, the ultrafine rectangular bar 1 rotates according to this rotational force. As shown in FIG. 6(b), when the clamping surface 8a of the vise clamp 8 comes in facial contact with the flat surface 1a of the side surface of the ultrafine rectangular bar 1, the ultrafine rectangular bar 1 stops rotating and keeps the stable position as pushed in a facial fashion from four directions by the vise clamps 8.

When a prescribe time passes after the vise clamp portion B begins its operation, as shown in FIG. 4, FIG. 5(e), the chuck driving means 3 operates to drive the chuck 2, thereby holding the ultrafine rectangular bar 1 again. The interval between the drive timing of the air cylinder 13 of the vise clamp portion B and the drive timing of the chuck driving means 3 can be a very short time, and from an external viewpoint, closing of the vise clamps 8 according to the drive of the air cylinder 13 is done nearly at the same time as holding of the ultrafine rectangular bar 1 by the chuck 2.

As shown in FIG. 4, FIG. 5(f), then, the motor 4, as a rotating means, and the motor 5b structuring the moving means 5 rotate at prescribed rotational numbers, respectively, and therefore, the chuck 2 rotates in a prescribed direction whereas the chuck portion A moves in a direction of arrow b.

According to rotations of the motors 4, 5b as described above, the ultrafine rectangular bar 1 is subject to the twisting processing with a prescribed pitch. The rotation number of the chuck 2 done by the motor 4 and the moving speed of the chuck portion A in the direction of arrow b done by the motor 5b are synchronized corresponding to the specification of the twisting process. The speed of the twisting process is set according to material and diameter of the ultrafine rectangular bar 1.

As described above, by moving the chuck 2 holding the ultrafine rectangular bar 1 in the direction of arrow a, by loosening the chuck 2 when the distal end 1b approaches to the stopper portion C, by contacting the distal end 1b of the ultrafine rectangular bar 1 to the stopper portion C where the chuck 2 continuously moves under this state, and by stopping the chuck 2 when the chuck 2 ends the prescribed movement, the protruding length of the ultrafine rectangular bar 1 from the chuck 2 can be regulated.

The ultrafine rectangular bar 1 can be rotated by the rotation force operating to the ultrafine rectangular bar when the vise clamps 8 contact to the corner of the ultrafine rectangular bar 1 upon approaching and contacting the vise clamps 8 of the vise clamp portion B to the ultrafine rectangular bar 1 in keeping the above state.

When the ultrafine rectangular bar 1 held by the vise clamps 8 of the vise clamp portion B is clamped again by the chuck 2, therefore, the protruding length of the ultrafine rectangular bar 1 from the chuck 2 and the held position are always substantially constant, and when the ultrafine rectangular bar 1 is subject to the twisting process after this operation, the position of the twisting start portion and the twisting length are not deviated at all.

As described above in detail, with the twisting apparatus according to this invention, the ultrafine rectangular bar can be held always with the same position and direction according to the vise clamp's contact to the ultrafine rectangular bar even where the ultrafine rectangular bar supplied from the exterior is held in any position and direction. Therefore, the twisting start positions of the ultrafine rectangular bars become substantially unified, and the products can be manufactured with stable quality.

By contacting the distal end of the ultrafine rectangular bar held by chuck to the stopper, the protruding length can be set substantially the same amount even where the ultrafine rectangular bar supplied from the exterior is protruded by a certain length or more.

The vise clamp can be smoothly and surely approached to the ultrafine rectangular bar by contacting a portion of the clamping surface of the vise clamp to the side surface of the adjacent vise clamp.

The foregoing description of a preferred embodiment of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined by the claims set forth below.

What is claimed is:

1. A twisting apparatus for an ultrafine rectangular bar, comprising:
    a chuck for holding a proximal end of the ultrafine rectangular bar;
    chuck driving means for holding or releasing the proximal end of the ultrafine rectangular bar by driving the chuck;
    at least two vise clamps structured to contact with and isolated from the ultrafine rectangular bar held by the chuck, each of the vise clamps having a pressing surface capable of contacting to a side surface of the ultrafine rectangular bar;
    vise clamp driving means for driving the vise clamps to move the vise clamps to contact with and isolated from the ultrafine rectangular bar;
    moving means for correlatively moving the chuck and the vise clamps along the axial center of the ultrafine rectangular bar held by the chuck; and
    rotating means for correlatively rotating the chuck and the vise clamps around the axial center of the ultrafine rectangular bar held by the chuck,
    wherein the chuck driving means and the vise clamp driving means are so controlled that, after the proximal end of the ultrafine rectangular bar is held by the chuck where the vise clamps are placed closely to the ultrafine rectangular bar, the chuck disengages ultrafine rectangular bar when the vise clamps contact to the ultrafine rectangular bar and then engages again the ultrafine rectangular bar, in a case where the vise clamps are approached closely to the ultrafine rectangular bar held by the chuck to twist the ultrafine rectangular bar upon isolating, as rotated correlatively, the chuck and the vise clamps from each other.

2. The twisting apparatus for an ultrafine rectangular bar according to claim 1, and further comprising a stopper contacting to the distal end of the ultrafine rectangular bar at a prescribed position on the axial center of the ultrafine rectangular bar held by the chuck, wherein the moving means, the chuck driving means, and the vise clamp driving means are so controlled that, where the vise clamp approaches closely and contacts to the ultrafine rectangular bar after the chuck holds the proximal end of the ultrafine rectangular bar, the chuck disengages from the ultrafine rectangular bar, and the distal end of the ultrafine rectangular bar is made in contact with the stopper upon moving correlatively the chuck and the stopper.

3. The twisting apparatus for an ultrafine rectangular bar according to claim 1, wherein the twisting apparatus includes four vise clamps disposed so that a portion of a clamp surface for clamping a side surface of the ultrafine rectangular bar can be in contact with a portion of the adjacent vise clamp.

4. An endodontic instrument having a spiral groove manufactured by twisting an ultrafine rectangular bar, the endodontic instrument manufactured by a manufacturing method comprising the steps of:
    holding a proximal end of the ultrafine rectangular bar with a chuck;
    making approach at least two of vise clamps to a side surface of the ultrafine rectangular bar;
    allowing rotation of the ultrafine rectangular bar by disengaging the chuck from the ultrafine rectangular bar when the vise clamps come in contact with the side surface of the ultrafine rectangular bar, to render a clamp surface of a distal end of the vise clamp in facial contact with a face of the side surface of the ultrafine rectangular bar;
    holding the ultrafine rectangular bar again by the chuck; and
    twisting the ultrafine rectangular bar in isolating the chuck from the vise clamps as correlatively rotating the chuck and the vise clamps.

5. The twisting apparatus for an ultrafine rectangular bar according to claim 2, wherein the twisting apparatus includes four vise clamps disposed so that a portion of a clamp surface for clamping a side surface of the ultrafine rectangular bar can be in contact with a portion of the adjacent vise clamp.

* * * * *